(12) United States Patent
Wang et al.

(10) Patent No.: US 11,307,160 B2
(45) Date of Patent: Apr. 19, 2022

(54) QUALITY DETECTION DEVICE, QUALITY DETECTION METHOD, AND INTEGRATED PROBE ASSEMBLY

(71) Applicant: HAN'S LASER TECHNOLOGY INDUSTRY GROUP CO., LTD, Shenzhen (CN)

(72) Inventors: Sheng Lin Wang, Shenzhen (CN); Hao Liu, Shenzhen (CN); Da Chang Hu, Shenzhen (CN); Yong Hu, Shenzhen (CN); Peng Fei Lei, Shenzhen (CN); Ji Guo Liu, Shenzhen (CN); Zuo Bin Xu, Shenzhen (CN); Yun Feng Gao, Shenzhen (CN)

(73) Assignee: HAN'S LASER TECHNOLOGY INDUSTRY GROUP CO., LTD, Shenzhen (CN)

( * ) Notice: Subject to any disclaimer, the term of this patent is extended or adjusted under 35 U.S.C. 154(b) by 1 day.

(21) Appl. No.: 16/854,917

(22) Filed: Apr. 22, 2020

(65) Prior Publication Data
US 2020/0249189 A1 Aug. 6, 2020

Related U.S. Application Data

(63) Continuation of application No. PCT/CN2018/113760, filed on Nov. 2, 2018.

(51) Int. Cl.
*G01N 27/20* (2006.01)
*G01N 33/207* (2019.01)
*G01N 27/04* (2006.01)

(52) U.S. Cl.
CPC ........... *G01N 27/20* (2013.01); *G01N 27/041* (2013.01); *G01N 33/207* (2019.01)

(58) Field of Classification Search
CPC .... G01N 27/20; G01N 33/207; G01N 27/041; G01R 1/073; G01R 27/02; G05B 19/05
See application file for complete search history.

(56) References Cited

U.S. PATENT DOCUMENTS

| 4,887,025 | A |   | 12/1989 | Re Fiorentin et al. |
| 4,888,546 | A | * | 12/1989 | Berry ..................... G01R 27/14 324/357 |

(Continued)

FOREIGN PATENT DOCUMENTS

| CN | 202974926 U | 6/2013 |
| CN | 204556732 U | 8/2015 |

(Continued)

OTHER PUBLICATIONS

International Search Report issued in corresponding international application No. PCT/CN2018/113760, dated Jul. 30, 2019.

(Continued)

*Primary Examiner* — Feba Pothen (57) ABSTRACT

The present disclosure relates to a welding quality detecting field, and specifically relates to a quality detection device. The quality detection device includes an integrated probe set, a driving module and a collecting module. The integrated probe set includes a plurality of integrated probe assemblies. The integrated probe assemblies are disposed in pairs and each integrated probe assembly includes a driving end and a collecting end. The driving end of one integrated probe assembly is matched with the driving end of another integrated probe assembly disposed in pairs with the one integrated probe assembly. The collecting end of one integrated probe assembly is matched with the collecting end of another integrated probe assembly disposed in pairs with the one integrated probe assembly.

9 Claims, 8 Drawing Sheets

(56) References Cited

U.S. PATENT DOCUMENTS

| | | | | |
|---|---|---|---|---|
| 5,488,308 | A * | 1/1996 | Kirka | B65B 7/18 |
| | | | | 324/500 |
| 6,583,386 | B1 * | 6/2003 | Ivkovich | B23K 9/0953 |
| | | | | 219/125.1 |
| 8,779,320 | B2 * | 7/2014 | Watanabe | B23K 11/115 |
| | | | | 219/55 |
| 9,766,053 | B1 * | 9/2017 | Okojie | G01B 7/02 |
| 10,983,081 | B2 * | 4/2021 | Redinger | G01N 27/041 |
| 2010/0140228 | A1 * | 6/2010 | Suzuki | B23K 31/125 |
| | | | | 219/117.1 |
| 2012/0090390 | A1 * | 4/2012 | Bell | G01N 3/58 |
| | | | | 73/104 |
| 2015/0069999 | A1 * | 3/2015 | Buschnakowski | G01N 27/07 |
| | | | | 324/149 |
| 2016/0098949 | A1 * | 4/2016 | Mo | G09G 3/006 |
| | | | | 324/755.01 |

FOREIGN PATENT DOCUMENTS

| | | |
|---|---|---|
| CN | 105202374 A | 12/2015 |
| CN | 106501320 A | 3/2017 |
| CN | 107344270 A | 11/2017 |
| CN | 107607592 A | 1/2018 |
| CN | 109596677 A | 4/2019 |

OTHER PUBLICATIONS

Written Opinion of the International Searching Authority for No. PCT/CN2018/113760.

* cited by examiner

QUALITY DETECTION DEVICE, QUALITY
DETECTION METHOD, AND INTEGRATED
PROBE ASSEMBLY

CROSS REFERENCE OF RELATED APPLICATIONS

The present application is a continuation-application of International (PCT) Patent Application No. PCT/CN2018/113760 filed on Nov. 2, 2018, the entire contents of which are hereby incorporated by reference.

TECHNICAL FIELD

The present disclosure relates to a field of welding quality detection, in particular to a quality detection device, a quality detecting method, and an integrated probe assembly.

BACKGROUND

Laser welding is a precise welding method, and refers to a welding method for forming a welding joint after melting of metal, in which uses a high-energy-density laser as a heat source. Welding precision of the laser welding is high, welding speed of the laser welding is fast, welding deformation of the laser welding is small, and the welding does not require a vacuum environment. In 1970s, the laser welding was mainly used for welding thin-materials, had a low-speed welding, and a welding process is of a heat-conduction type, namely a surface of a workpiece is heated by laser radiation. Surface heat is diffused to the interior through heat conduction. The workpiece is melted by controlling parameters of a laser pulse such as a width, energy, peak power, and repetition frequency to form a specific weld pool. Due to specific advantages of the laser welding, laser welding is successfully used in precise welding of micro-size and small-size parts.

With development of laser equipment, the welding speed of the laser welding is getting faster and faster. For example, welding speed of a scanning galvanometer can reach a driving probe 200 mm/s, which causes enterprises make higher requirements for efficiency of welding quality detection. Common detecting methods include magnetic powder flaw detection, penetration flaw detection, ultrasonic flaw detection, and radiographic detection.

The magnetic powder flaw detection is non-destructive detection method for detecting defects which are at a surface or near the surface of a ferromagnetic material through accumulation of magnetic powder in leakage magnetic field near the defects. The magnetic powder flaw detection is a flaw detection method that makes the workpiece made of magnetic materials, such as iron and steel, magnetized, displays surface defects and near-surface defects of detected objects by utilizing characteristics of magnetic flux leakage in a defective part of the workpiece that is capable of adsorbing the magnetic powder according to distribution of the magnetic powder. This method has low efficiency and pollutes the workpiece.

The penetration flaw detection is a non-destructive detection method for detecting surface defects of a material by utilizing the capillary phenomenon, and this method has low efficiency.

Ultrasonic flaw detection is a method that checks part defects by characteristics of utilizing ultrasonic energy to penetrate into a deep portion of a metal material, and generating reflection at a cross-sectional edge when leaving a cross section into another cross section. When an ultrasonic beam passes through a surface of the part, enters an interior of the metal material from a probe, and encounters the defects and a bottom surface of the part, reflected waves are respectively generated. Pulse waveforms are formed on a fluorescent screen. Position and size of the defects are determined according to the pulse waveforms. This method has a high requirement on operating personnels and is not suitable for parts having a cavity structure.

Radiographic detection is a method that checks internal defects of a welded seam by utilizing certain kind of rays, and this method is relatively high in equipment cost and relatively slow in detecting speed.

Resistance testing welded seam quality is a novel welding quality detecting method. In current research results, there are generally four parallel probes for detecting. To be specific, two probes in an outer side are set as driving probes to release pulse current, two probes in an inner side are set as collecting probes on two sides of the welded seam to collect voltage variation of the two sides of welded seam, and welded seam resistance is calculated by a resistance gauge. Most detection is performed by simultaneously sliding the four probes to detect a whole welded seam resistance. Although sliding the four probes to detect whole welded seam resistance is feasible in principle, many problems exist in the actual detection process. For example, sliding of the probes causes scratching of surface of the workpiece, and abrasion of the probes caused by multiple slidings influences a detecting result. Specifically a sliding detection has a very high surface roughness requirement of the workpiece, so that an abnormal numerical value is easily generated, and reliability of the detecting result is severely interfered. A probe sliding detection further has problems such as the probes easily bend to generate deformation, sliding speed of the probes is low, and detecting efficiency is slow. Thus, detecting the welded seam resistance by sliding the probes to judge welded seam quality is difficult to apply to actual production.

There are mature resistance gauges in the present market, such as micro-resistance detectors of companies like APPLENT and HIOKI. Testing principles of the resistance gauges are similar, which uses four-wire measuring resistance. Two driving wires are connected with a resistance gauge driving port (Drive) and the probes, and other two collecting wires are connected with a collecting port (Sense). The probes connected with the driving wires release direct-current on the two sides of the welded seam. The probes connected with the collecting wires collects voltage changes of the two sides of a welded seam, and calculates a welded seam resistance by the resistance gauge. However, the present instrument channel only has two driving ports and two collecting ports to form a detecting channel, which can only detect the resistance at a certain position of the welded seam. It is hard to rapidly detect the whole welded seam so as to judge the welding quality.

SUMMARY

An object of the present disclosure is to provide a quality detection device to solve the above problem about defects caused by single-channel detection, such as scratches on workpiece surface, low detecting efficiency and low reliability.

An object of the present disclosure is to provide a quality detecting system to solve the above problem about defects caused by single-channel detection, such as scratches on workpiece surface, low detecting efficiency and low reliability.

An object of the present disclosure is to provide a quality detecting method to solve the above problem about defects caused by single-channel detection, such as scratches on workpiece surface, low detecting efficiency and low reliability.

A technical solution to solve the technical problem thereof adopted the present disclosure.

The present disclosure provides a quality detection device to solve the technical problem. The quality detection device includes an integrated probe set, a driving module and a collecting module. The integrated probe set includes a plurality of integrated probe assemblies. The integrated probe assemblies are disposed in pairs and each of the integrated probe assemblies includes a driving end and a collecting end. The driving end of one integrated probe assembly is matched with the driving end of another integrated probe assembly disposed in pairs with the one integrated probe assembly, and the collecting end of one integrated probe assembly is matched with the collecting end of another integrated probe assembly disposed in pairs with the one integrated probe assembly. The driving module releases current to form a current loop with a conductor by driving ends, where the driving ends abut against the conductor. The collecting module obtains a resistance value of an area of the current loop formed in the conductor, where the collecting ends abut against the conductor.

The present disclosure provides a quality detecting method solving the technical problem through the quality detection device, which including steps:

respectively abutting the integrated probe assemblies in pairs against two sides of a welded seam on the conductor;

releasing a current to form a current loop between a conductor and the driving ends abutting against the conductor;

abutting collecting ends against the conductor, obtaining an electrical information of an area of the current loop formed in the conductor, and forming a plurality of scanning channels; and converting the collected electrical information into a resistance value and obtaining a quality of the welded seam.

The present disclosure provides a quality detecting system solving the technical problem through the quality detection device. The quality detecting system includes the quality detection device and a moving assembly configured to fix integrated probe assemblies. The moving assembly is connected with a support or the conductor to realize relative movement of the support and the conductor. The support includes fixing ends disposed in two rows, and the fixing ends respectively fix the corresponding integrated probe assemblies. The moving assembly drives the support to move such that the integrated probe assemblies disposed in pairs abut against two sides of the welded seam of the corresponding conductor.

The present disclosure provides an integrated probe assembly to solve the technical problem. The integrated probe assembly includes a driving end and a collecting end integrated together with the driving end, and the integrated probe assembly is disposed in pairs. The driving end of one integrated probe assembly is matched with the driving end of another integrated probe assembly disposed in pairs with the one integrated probe assembly, and the collecting end of one integrated probe assembly is matched with the collecting end of another integrated probe assembly disposed in pairs with the one integrated probe assembly. The driving end is connected with an external driving module. The external driving module releases current, and the driving end receives and transmits the current to form the current loop with the conductor by cooperating another driving end, where the two driving ends abut against the conductor. The collecting end is connected with an external collecting module. Under an effect of the external collecting module, the collecting end obtains the electrical information of the area of the current loop formed in the conductor by cooperating another collecting end, where the two collecting ends abut against the conductor.

Compared with the prior art, the present disclosure provides a quality detection device, a quality detecting system and a quality detecting method based on the welded seam. Rapidly detecting of welding quality of the whole welded seam is realized by cooperation of the integrated probe set, the driving module and the collecting module. Detection of a plurality of scanning channels does not require to slide probes, so that a detection workpiece is not scratched, and requirement on roughness of workpiece surface is low. Furthermore, probes do not need to slide, which reduce abnormal fluctuation and makes reliability of the detection higher. Furthermore, resistance is obtained by rapidly scanning the plurality of channels, which makes detecting efficiency higher and is more suitable for large-batch detection of the welded seam. Furthermore, the present disclosure is with advantages of high detecting speed, high efficiency, none of pollution, and well stability, which expands the quality detecting method of a laser welding, the welded seam, and the welding. Furthermore, the present disclosure optimizes a probe structure to adapt widths of different detecting conductors by the integrated probe assemblies.

DETAILED DESCRIPTION

The embodiments of the present disclosure are described below with referring to the accompanying drawings.

Figure 1:
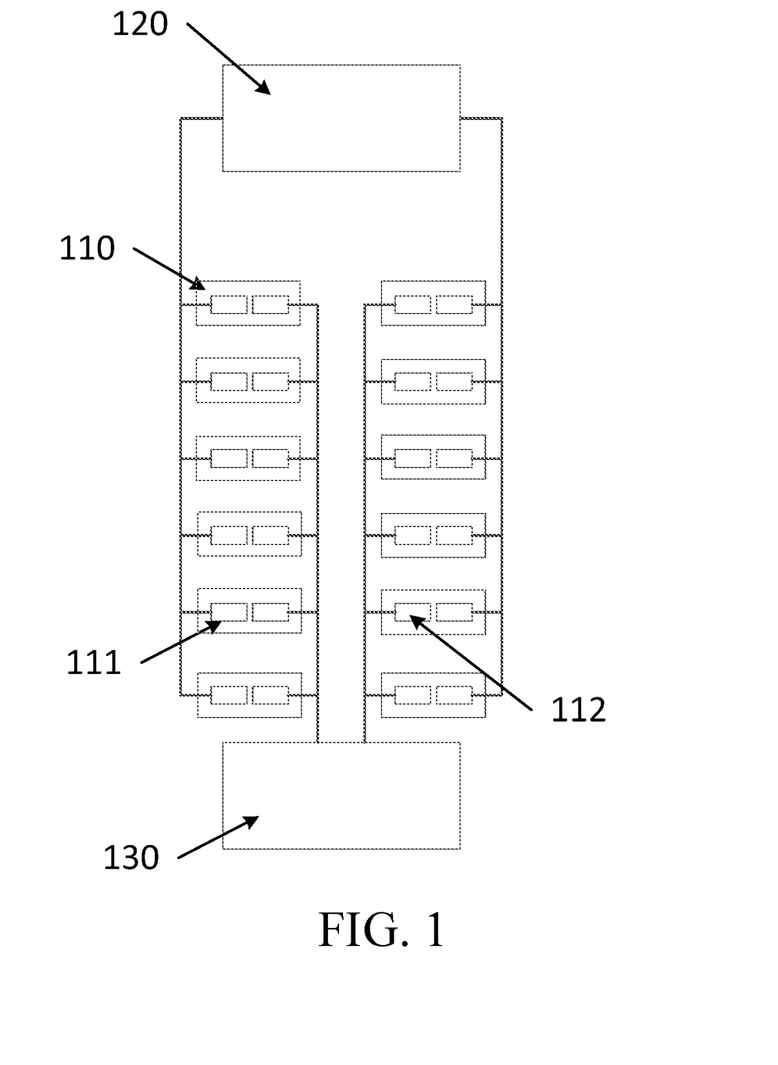
FIG. 1 is a principle schematic diagram of a quality detection device of the present disclosure.
Figure 2:
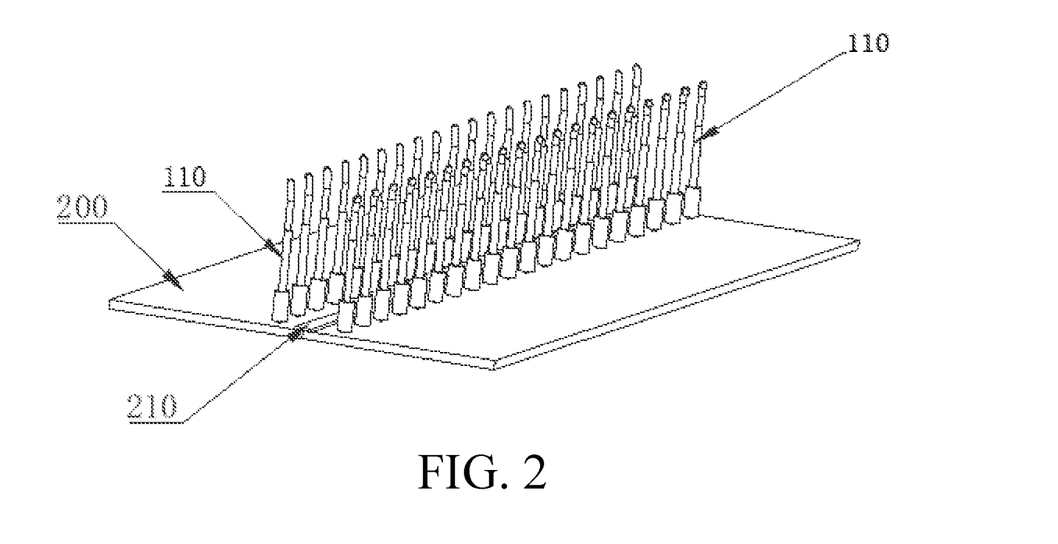
FIG. 2 is a structural schematic diagram of a quality detection device based on a parallel welding conductor of the present disclosure.
Figure 3:
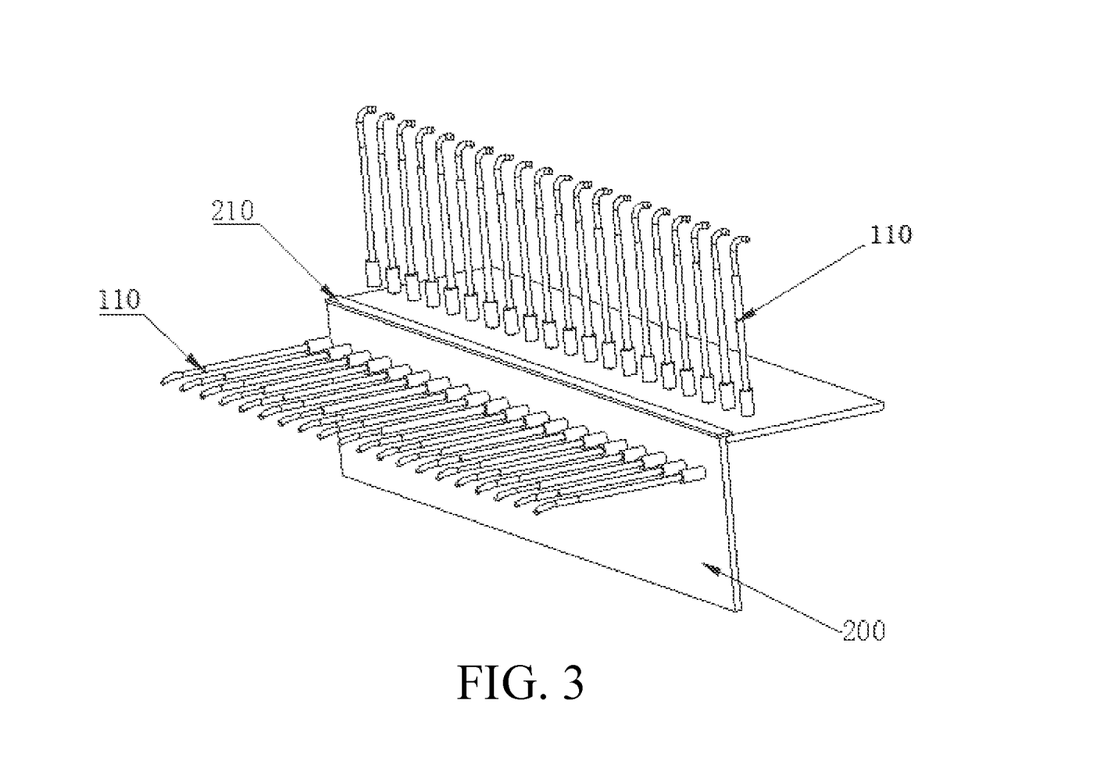
FIG. 3 is a structural schematic diagram of a quality detection device based on a vertical welding conductor of the present disclosure.

As shown in FIGS. 1-3, the present disclosure provides one embodiment of a quality detection device.

A quality detection device, the quality detection device includes an integrated probe set, a driving module 130 and a collecting module 120. The integrated probe set includes a plurality of integrated probe assemblies 110. The integrated probe assemblies 110 are disposed in pairs and each of the integrated probe assemblies includes a driving end 112 and a collecting end 111. The driving end 112 of one integrated probe assembly 110 is matched with the driving end 112 of another integrated probe assembly 110 disposed in pairs with the one integrated probe assembly 110. The collecting end 111 of one integrated probe assembly 110 is matched with the collecting end 111 of another integrated probe assembly 110 disposed in pairs with the one integrated probe assembly 110. The driving module 130 releases current to form a current loop with a conductor 200 by the driving end 112, where the driving end 112 abuts against the conductor 200. The collecting module 120 obtains a resistance value of an area of the current loop formed in the conductor 200, where the collecting end 111 abuts against the conductor 200.

Furthermore, the plurality of integrated probe assemblies 110 are disposed in two rows. The integrated probe assemblies 110 in one row are disposed in pairs with the integrated probe assemblies 110 in the other row. Two integrated probe assemblies 110 respectively disposed in two rows are set as a pair. The driving ends 112 of the two integrated probe assemblies 110 form a driving current loop by the driving module 130. The collecting ends 111 of the two integrated probe assemblies 110 form a collecting current loop by the collecting module 120. And multiple pairs of the integrated probe assemblies 110 form a plurality of scanning channels. And, the integrated probe assemblies 110 in two rows are respectively disposed on two sides of the welded seam of the conductor 200 to form the plurality of scanning channels, so that quality detection of the welded seam is performed.

Specifically, referring to FIG. 2 and FIG. 3, a welded conductor 200 is provided. The integrated probe assemblies 110 disposed in two rows abut against the conductor 200, and the integrated probe assemblies 110 are disposed on two sides of the welded seams 210 of the conductor 200. An interval of each row of the integrated probe assemblies 110 in pairs is appropriate, that is, the interval is not too large or too small. If the interval is too large, measurement accuracy is insufficient, and if the interval is too small, the integrated probe assemblies beside each other easily generate interference to influence a measurement structure, or resource waste is caused. And, when both of the driving ends 112 and the collecting ends 111 abut against corresponding position of the conductor 200, the driving module 130 is controlled to electrify the driving ends 112, and forms the current loops with the conductor 200. The current loops pass through the welded seams 210, and then voltage value of corresponding position of the welded seams 210 is collected. The electrical information of the conductor 200 of this position is obtained by the collecting ends 111. Quality of the welded seams 210 is determined according to the electrical information.

And, the quality detection device further includes a master-control module connected with the collecting module 120. The master-control module obtains the electrical information obtained by the collecting module 120, such as the voltage value. The master-control module obtains the resistance value of the welded seam 210 according to the voltage value and determines the quality of the welded seam 210 according to the resistance value.

Furthermore, the integrated probe assemblies 110 in pairs are operated in sequence until all the probe assemblies 110 realize a collection of the electrical information. For example, the driving ends 112 are electrified in sequence, then parameters are collected by corresponding collecting ends 111 to realize multiplexing of the driving module 130 and the collecting module 120. Or the driving ends 112 are simultaneously electrified and the parameters are collected by the corresponding collecting ends 111 to work simultaneously, and quality detecting efficiency is improved.

Figure 4:
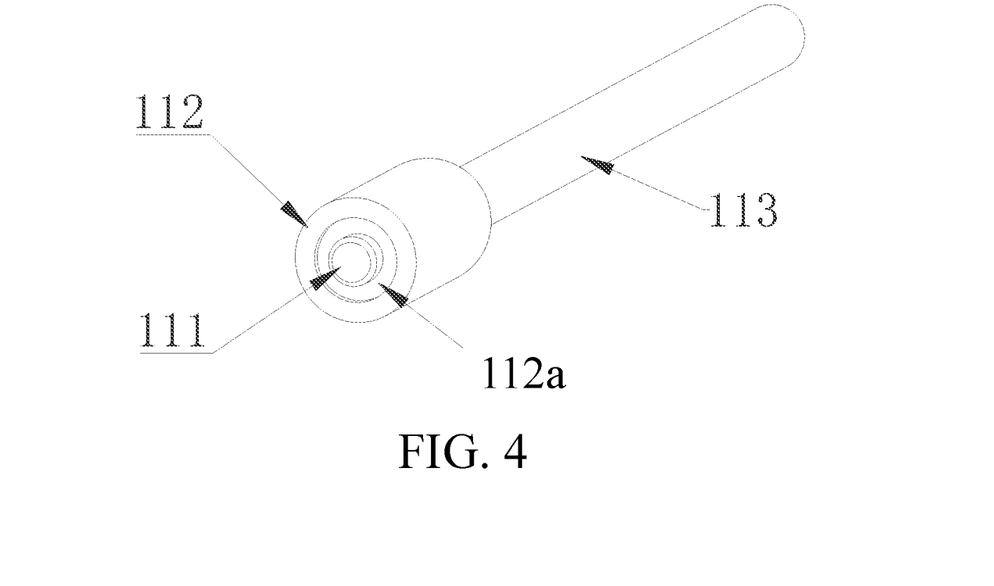
FIG. 4 is a structural schematic diagram of an integrated probe assembly of first scheme of one embodiment of the present disclosure.
Figure 5:
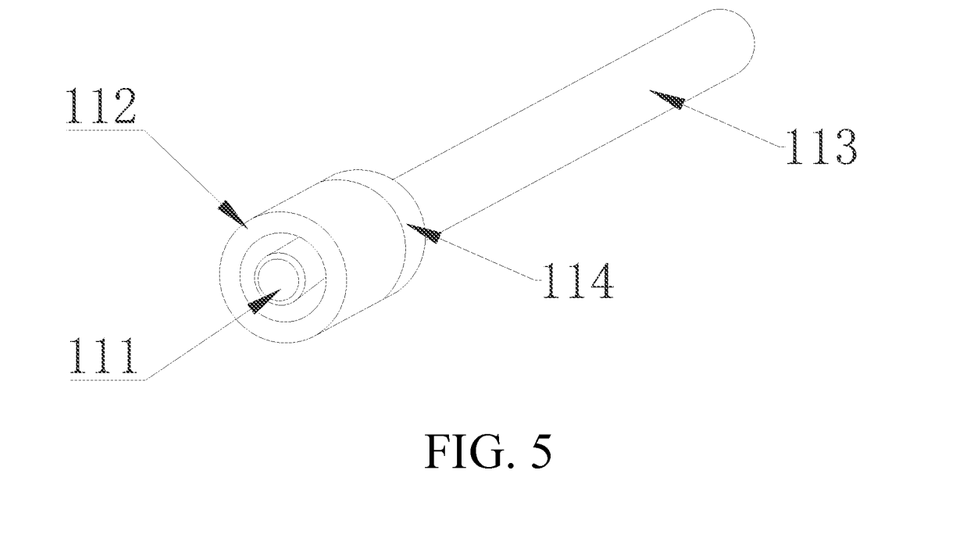
FIG. 5 is a structural schematic diagram of an integrated probe assembly of second scheme of one embodiment of the present disclosure.
Figure 6:
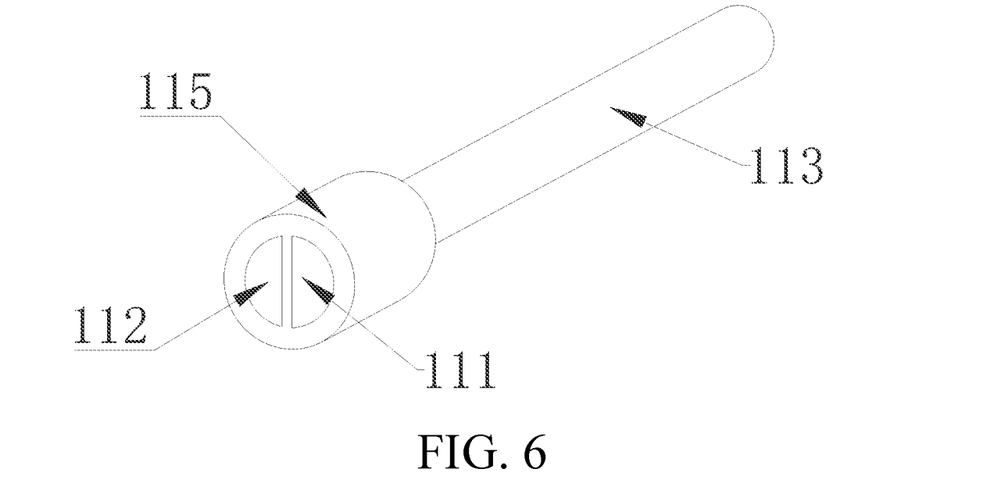
FIG. 6 is a structural schematic diagram of an integrated probe assembly of third scheme of one embodiment of the present disclosure.

As shown in FIGS. 4-6, the present disclosure provides one embodiment of an integrated probe assembly.

In the embodiment, the present disclosure provides three schemes of the integrated probe assembly. According to the integrated probe assembly, the driving end 112 and the collecting end 111 are integrated, which simplify a structure, facilitate detection, and reduce error rate. Specifically, the driving end 112 and the collecting ends 111 are required to simultaneously abut against the conductor 200. Otherwise poor contact of the integrated probe assembly is easily generated. Furthermore, an area of the conductor contacting the integrated probe assembly is small to be convenient to detect a narrow-edge welded seam.

Of course, the driving end 112 and the collecting end 111 are disposed in an insulating manner so as to prevent contact short circuits.

In first scheme, the integrated probe assembly 110 includes a first probe disposed on an outer side of the integrated probe assembly 110 and a second probe disposed in an inner side of the integrated probe assembly 110. An end face of the first probe and an end face of the second probe are disposed in a same level when the integrated probe assembly 110 abuts against the conductor. The first probe is one of driving end 112 and the collecting end 111, and the second probe is the other one of the driving end 112 and the collecting end 111.

Furthermore, referring to FIG. 4, an end-part groove 112a is disposed on the first probe, and the second probe is disposed in the end-part groove 112a. Furthermore, the present disclosure provides one integrated probe assembly 110 including the driving end 112 and the collecting end 111 integrated together with the driving end 112. The driving end 112 is connected with an external driving module, the external driving module releases current, and the driving end 112 receives and transmits the current to form the current loop with the conductor by cooperating another driving end 112, where the two driving ends 112 abut against the conductor. The collecting end 111 is connected with an external collecting module. Under an effect of the external collecting module, the collecting end 111 obtains the electrical information of the area of the current loop formed in the conductor by cooperating another collecting end 111, where the two collecting ends 111 abut against the conductor. The integrated probe assembly 110 includes a driving probe and a collecting probe. The driving probe is disposed on an outer side of the integrated probe assembly 110 as the driving end 112 and the collecting probe is disposed in an inner side of the integrated probe assembly 110 as the collecting end 111. An end face of the driving probe and an end face of the collecting probe are disposed in the same level when the integrated probe assembly 110 abuts against the conductor.

Specifically, a bottom of the end-part groove 112a is provided with an installing structure configured to install the collecting probe, and the collecting probe is insulated from the driving probe by an insulating block. Furthermore, the end-part groove 112a is provided with a channel connecting with an external connecting wire or a connecting conductor. Furthermore, the external connecting wire or the connecting conductor is insulated from the driving probe. Furthermore, a detecting end of the collecting probe and the detecting end of the driving probe are disposed in the same level at least when the detecting end of the collecting probe abuts against the conductor 200.

In second scheme, referring to FIG. 5, basing on the first scheme, the first probe is of an annular tubular structure and the second probe is disposed in a hollow structure of the first probe. The first probe is one of the driving end 112 and the collecting end 111, and the second probe is the other one of the driving end 112 and the collecting end 111.

Specifically, the integrated probe assembly 110 further includes a substrate 114 disposed on a bottom of the integrated probe assembly 110, and the collecting probe is disposed on the substrate 114. Furthermore, the driving probe is in an annular hollow tubular shape, and the collecting probe is of a cylindrical structure. And, the detecting end of the collecting probe and the detecting end of the driving probe are disposed in the same level at least when the detecting end of the collecting probe abuts against the conductor 200.

In third scheme, referring to FIG. 6, the integrated probe assembly 110 includes the first probe and the second probe, where the first probe and the second probe are disposed in two rows and the first probe is insulated from the second probe. Specifically, the integrated probe assembly further includes a substrate 115. Both of the first probe and the second probe are fixed on the substrate 115. The first probe is one of the driving end 112 and the collecting end 111, and the second probe is the other one of the driving end 112 and the collecting end 111.

In the embodiment, in the first scheme and the second scheme, the integrated probe assembly further includes an elastic piece. The elastic piece is disposed on a bottom of the second probe. The second probe performs a telescopic movement at a horizontal position of an end surface of the first probe when the elastic piece is driven by external force. Or, the elastic piece is disposed on a bottom of the first probe. The first probe performs the telescopic movement at the horizontal position of an end surface of the second probe when the elastic piece is driven by external force.

Generally, the first probe extends out of an opening of the second probe under an effect of the elastic piece, if the integrated probe assembly 110 abuts against the conductor 200, the first probe performs a retract movement when the elastic piece is driven by a pressure to make the first probe and the second probe abut against the conductor 200.

And, in the third scheme, the integrated probe assembly 110 further includes an elastic piece. The elastic piece is disposed on the substrate 115 and an end part of the first probe. Or, the elastic piece is disposed on the substrate 115 and an end part of the second probe. Making the driving probe and the collecting probe dispose in the same level is realized by the elastic piece.

In the embodiment, the integrated probe assembly 110 further includes an extension end 113 disposed on a bottom of the integrated probe assembly. The extension end 113 wraps the first connecting wire and the second connecting wire. The first connecting wire is electrically connected with the driving end 112 and the driving module respectively, and the second connecting wire is electrically connected with the collecting end 111 and the collecting module respectively.

In the embodiment, in the first scheme, the first probe serves as the driving end 112, and the second probe serves as the collecting end 111, so that current flowing among the driving ends 112 is not affected and accuracy is improved. Furthermore, the electrical information is accurately obtained by the collecting end 111 disposed inside to realize accurate degree of collecting data.

Figure 7:
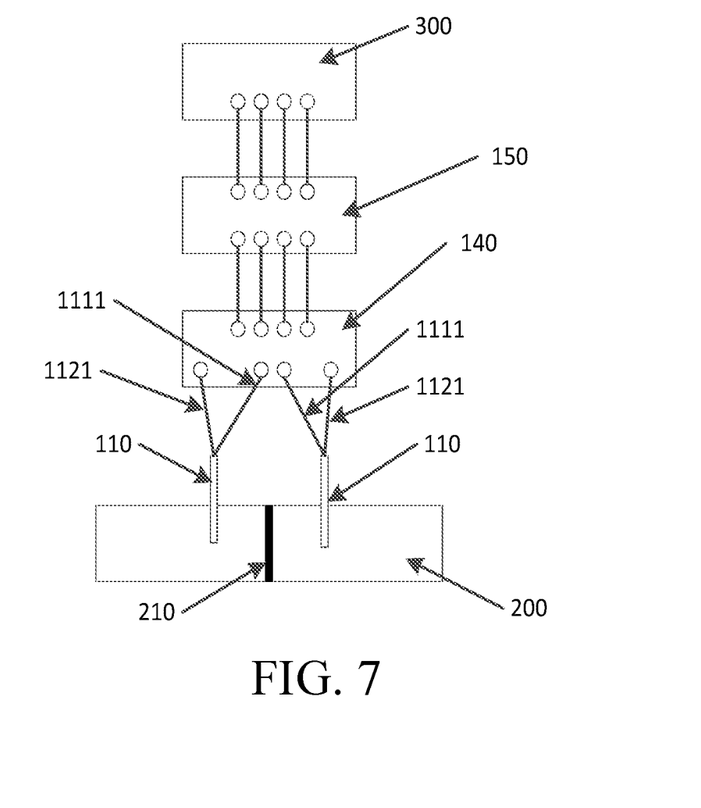
FIG. 7 is a structural schematic diagram of a quality detection device of the present disclosure.
Figure 8:
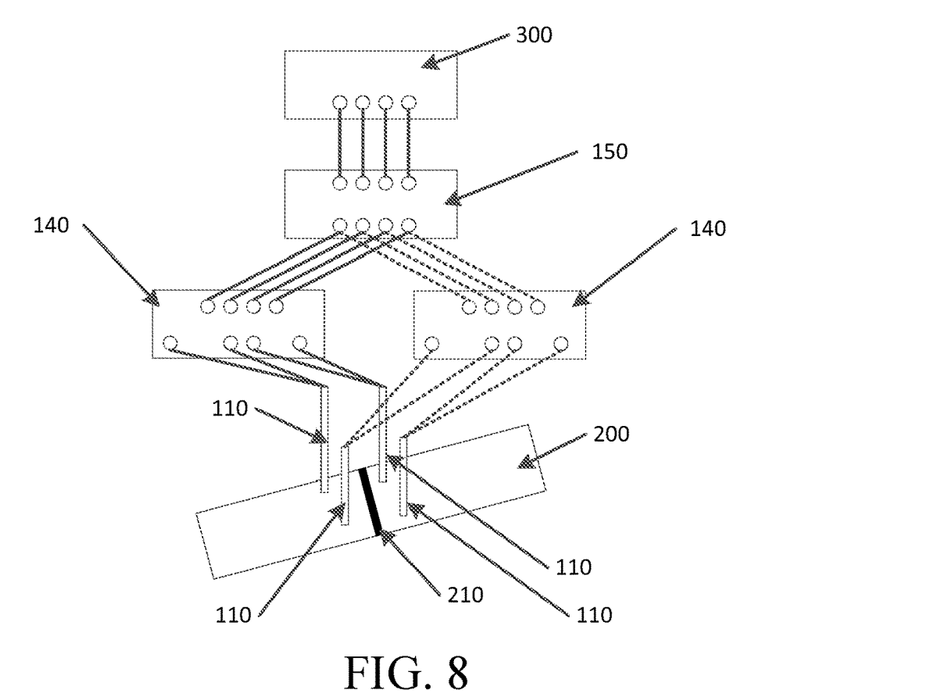
FIG. 8 is a structural schematic diagram of FIG. 7 based on a plurality of switching modules.

As shown in FIG. 7 and FIG. 8, the present disclosure provides one embodiment of circuit control.

The quality detection device further includes an integrated circuit with a plurality of switching modules 140. The matched driving ends 112 and collecting ends 111 are respectively connected to the driving module 130 and the collecting module 120 by a switching module 140. The integrated circuit sequentially turns on the switching module 140 and enables the driving module 130 to release current to form the current loop with the conductor 200 by the driving ends 1120, where the driving ends 112 abut against the conductor 200; and the collecting module 120 obtains the resistance value of the area of the current loop formed in the conductor 200, where the collecting ends 111 abut against the conductor 200.

Furthermore, the integrated circuit includes a programmable logic controller (PLC) module 150 configured to transmit data and relays forming the switching modules 140. The PLC module 150 is respectively connected with the driving module 130, the collecting module 120, and a plurality of relays. Each relay is connected with two driving ends 112 and two collecting ends 111.

Specifically, the integrated probe assemblies 110 respectively abut against the conductor 200 and are disposed on two sides of the welded seam 210. When the integrated probe assemblies 110 abut against the conductor 200, the driving ends 112 and the collecting ends 111 contact surface of the conductor 200 to realize electric connection. One integrated probe assembly 110 is connected with a first driving interface of one switching module 140 by a driving wire 1121, and connected with a first collecting interface of the switching module 140 by a collecting wire 1111, the other integrated probe assembly 110 disposed in pairs with the one integrated probe assembly is connected with a second driving interface of the switching module 140 and a second collecting interface of the switching module 140 by the driving wire 1121 and the collecting wire 1111, and the data is respectively transferred to the driving module 130 and the collecting module 140 by the PLC module 150. The working process is as following:

first, one switching module 140 is turned on, and other switching modules 140 are closed;

second, the driving module 130 outputs a current value to the corresponding driving ends 112 by the switching module 140 which is turned on to form the current loop; that is, driving module 130—PLC module 150 (driving output end)—switching module 140 (outputting from first driving interface)—driving end 112 (driving end connected with first driving interface)—conductor 200—welded seam 210—conductor 200—driving end 112 (driving end connected with second driving interface)—switching module 140 (inputting from second driving interface)—PLC module (driving input end)—driving module 130; and third, the collecting module 120 obtains a voltage value on the two sides of the welded seam by the switching module 140 which is turned on, and transfers the voltage value into a resistance value.

In one embodiment, the driving module 130 and the collecting module 120 are integrated into a micro resistance meter 300. The micro resistance meter 300 includes a driving system and a collecting system. The driving system is configured to output current and connects with the driving module 130, and the collecting system is configured to collect electrical information and connects with the collecting module 120.

A control principle is as follows: the relay is switched by the relay (one relay is disconnected, and the other is simultaneously disconnected), the micro resistance meter continuously scans and detects the integrated probe assemblies 110 connected with the relays, so that the resistance value of the welded seam between each pair of the integrated probe assemblies 110 is obtained.

Figure 9:
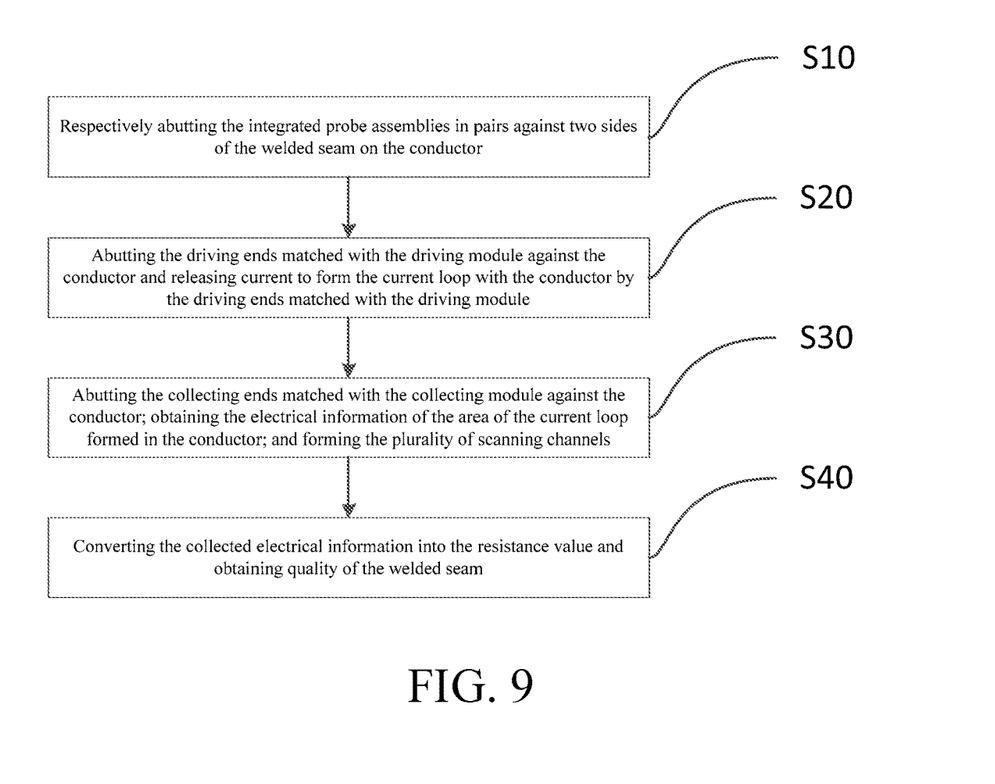
FIG. 9 is a flowchart of a quality detecting method of the present disclosure.
Figure 10:
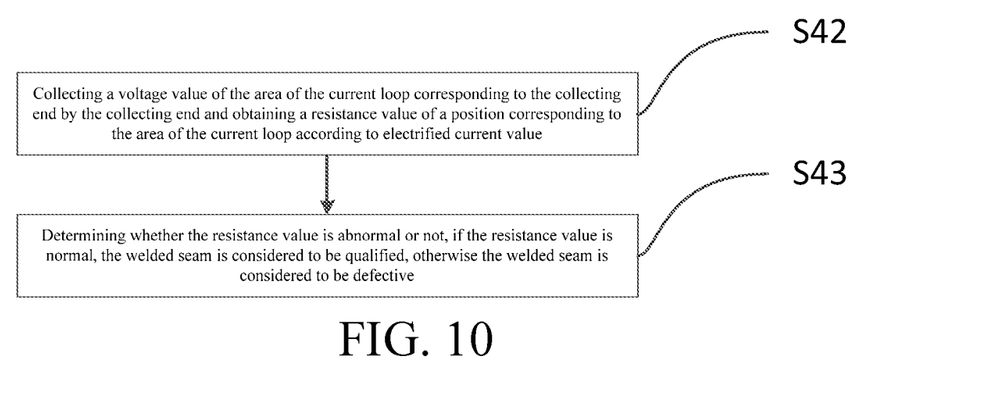
FIG. 10 is a flow schematic diagram of a quality detecting method basing on determining whether resistance value is abnormal or not of the present disclosure.
Figure 11:
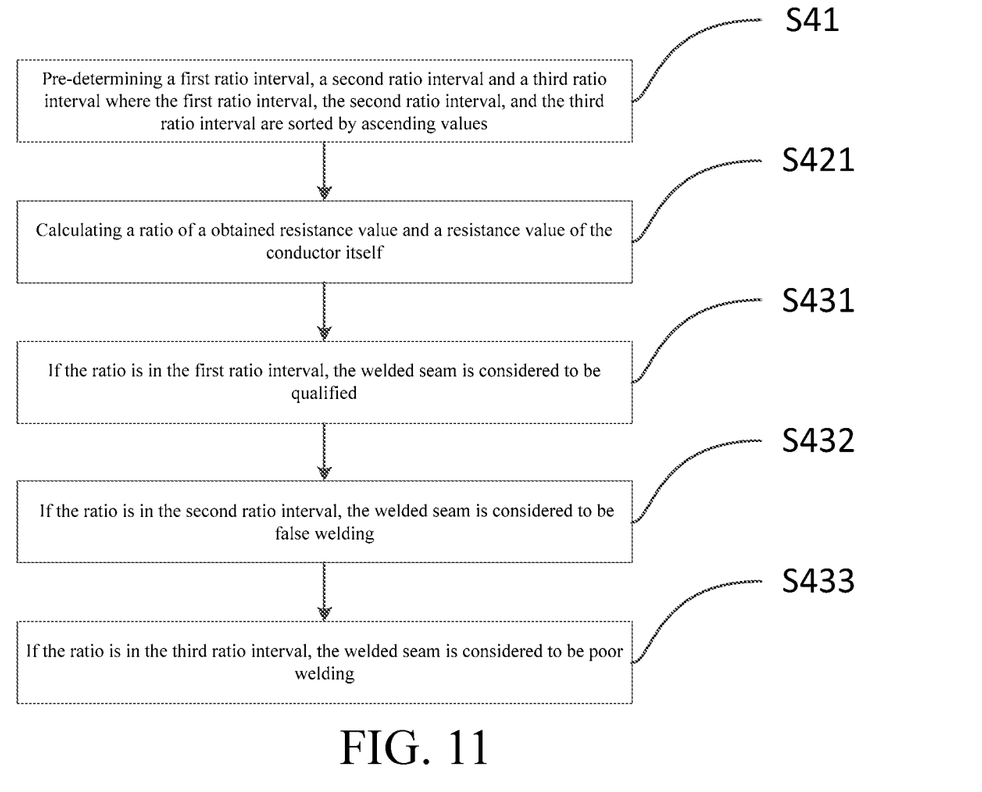
FIG. 11 is a flow schematic diagram of a quality detecting method basing on calculating ratio of obtained resistance value and resistance value of a conductor itself of the present disclosure.

As shown in FIGS. 9-11, the present disclosure provides one embodiment of a quality detecting method based on the welded seam.

A quality detecting method based on the welded seam, the quality detecting method is realized by the quality detection device, including steps:

S10, respectively abutting the integrated probe assemblies in pairs against two sides of the welded seam on the conductor;

S20, releasing a current to form a current loop between a conductor and the driving ends abutting against the conductor;

S30, abutting the collecting ends against the conductor; obtaining the electrical information of the area of the current loop formed in the conductor; and forming the plurality of scanning channels; and S40, converting the collected electrical information into the resistance value and obtaining quality of the welded seam.

Specifically, the integrated probe assemblies 110 abut against the conductor 200 and respectively disposed in rows on the two sides of the welded seam 210 on the conductor 200. The driving ends 112 are respectively disposed in alignment on two sides of the welded seam 210, and the collecting ends 112 are respectively disposed in alignment on two sides of the welded seam 210. The driving module 130 electrifies the driving ends 112, and the current loop is formed among the driving ends 112, the conductor 200, and the welded seam 210. The collecting module 120 collects the electric information of corresponding area of the current loop by the collecting ends 111 to form the plurality of scanning channels. A master-control module obtains the quality of the welded seam 210.

In the embodiment, steps of quality detecting method further include:

S42, collecting a voltage value of the area of the current loop corresponding to the collecting end by the collecting end and obtaining a resistance value of a position corresponding to the area of the current loop according to electrified current value; and S43, determining whether the resistance value is abnormal or not, if the resistance value is normal, the welded seam is considered to be qualified, otherwise the welded seam is considered to be defective.

Furthermore, steps of determining the quality of the welded seam include:

S41, pre-determining a first ratio interval, a second ratio interval and a third ratio interval, where the first ratio interval, the second ratio interval, and the third ratio interval are sorted by ascending values;

S421, calculating a ratio of a obtained resistance value and a resistance value of the conductor itself;

S431, if the ratio is in the first ratio interval, the welded seam is considered to be qualified;

S432, if the ratio is in the second ratio interval, the welded seam is considered to be false welding; and S433, if the ratio is in the third ratio interval, the welded seam is considered to be poor welding.

Furthermore, the first ratio interval ranges from 90% to 110%; the second ratio interval ranges from 110% to 210%; and the third ratio interval is above 210%.

Corresponding step, such as the step of S431, the step of S432, and the step of S433, is performed according to a result obtained after performing the step of S421.

Figure 12:
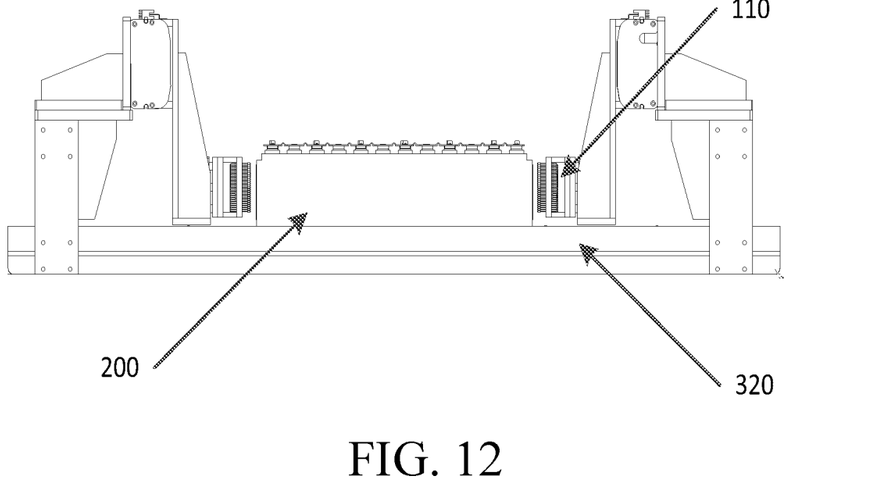
FIG. 12 is a structural schematic diagram of a quality detecting system of the present disclosure.
Figure 13:
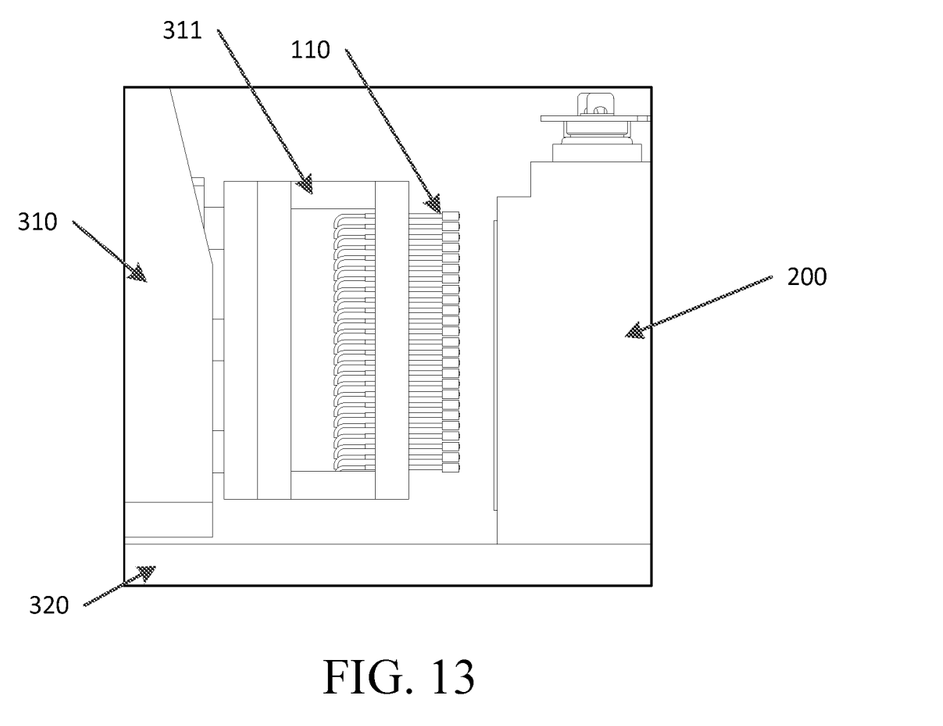
FIG. 13 is a local structural schematic diagram of FIG. 12.
Figure 14:
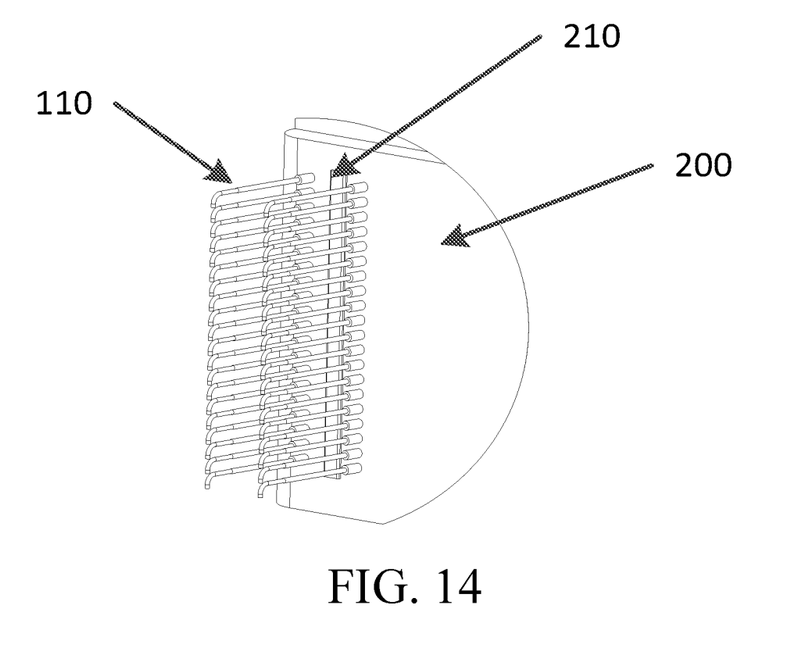
FIG. 14 is a structural schematic diagram of the present disclosure where integrated probe assemblies abut against a conductor.

As shown in FIGS. 12-14, the present disclosure provides one embodiment of a quality detecting system.

The quality detecting system includes the quality detection device and a moving assembly configured to fix integrated probe assemblies. The moving assembly is connected with a support 310 or the conductor 200 to realize relative movement of the support 310 and the conductor 200. The support 310 includes fixing ends 311 disposed in two rows, the fixing ends 311 respectively fix the corresponding integrated probe assemblies 110. And the moving assembly drives the support 310 to move such that the integrated probe assemblies disposed in pairs abut against two sides of the welded seam 210 of the corresponding conductor.

In the present embodiment, referring to FIG. 13, the quality detecting system includes a workbench 320, a conductor clamping end disposed on a center of the workbench 320, and the support 310 disposed on two sides of the workbench. The moving assemblies are disposed between the workbench 320 and the support 310 to drive the support 310 to move inwards or outwards along the workbench 320.

It should be understood that the specific embodiments described herein are only used to explain the present disclosure and are not intended to limit the present disclosure. Equivalent changes or modifications made by a scope of the present disclosure are covered by the present disclosure.

What is claimed is:

1. A quality detection device, comprising an integrated probe set, a driving module, and a collecting module; wherein the integrated probe set comprises a plurality of integrated probe assemblies; the integrated probe assemblies are disposed in pairs and each of the integrated probe assemblies comprises a driving end and a collecting end; the driving end of one integrated probe assembly is matched with the driving end of another integrated probe assembly disposed in pairs with the one integrated probe assembly; the collecting end of one integrated probe assembly is matched with the collecting end of another integrated probe assembly disposed in pairs with the one integrated probe assembly; the driving module releases current to form a current loop with a conductor by driving both of the driving ends of the one integrated probe assembly and the another integrated probe assembly, where the driving ends abut against the conductor; the collecting module obtains a resistance value of an area of the current loop formed in the conductor, where the collecting ends abut against the conductor;

wherein the integrated probe assemblies comprise a first probe disposed on an outer side of the integrated probe assemblies and a second probe disposed in an inner side of the integrated probe assemblies; an end face of the first probe and an end face of the second probe are disposed in a same level when the integrated probe assemblies abut against the conductor; wherein the first probe is one of the driving end and the collecting end; and the second probe is the other one of the driving end and the collecting end;

wherein the quality detection device further comprises a moving assembly configured to fix the integrated probe assemblies; the moving assembly is connected with a support or the conductor to realize relative movement of the support and the conductor; the support comprises fixing ends disposed in two rows, the fixing ends respectively fix the corresponding integrated probe assemblies; and the moving assembly drives the support to move such that the integrated probe assemblies disposed in pairs abut against two sides of a welded seam of the corresponding conductor;

wherein the quality detection device comprises a workbench, a conductor clamping end disposed on a center of the workbench, and the support is disposed on two sides of the workbench; the moving assembly is disposed between the workbench and the support to drive the support to move inwards or outwards along the workbench.

2. The quality detection device according to claim 1, wherein the integrated probe assemblies are disposed in two rows; the integrated probe assemblies in one row are disposed in pairs with the integrated probe assemblies in the other row.

3. The quality detection device according to claim 1, wherein an end-part groove is disposed on the first probe and the second probe is disposed in the end-part groove.

4. The quality detection device according to claim 1, wherein the first probe is of an annular tubular structure and the second probe is disposed in a hollow structure of the first probe.

5. The quality detection device according to claim 1, wherein the quality detection device further comprises an integrated circuit with a plurality of switching modules; the matched driving ends and collecting ends are respectively connected to the driving module and the collecting module by a switching module; the integrated circuit sequentially turns on the switching module and enables the driving module to release current to form the current loop with the conductor by the driving ends where the driving ends abut against the conductor; and the collecting module obtains the resistance value of the area of the current loop formed in the conductor, where the collecting ends abut against the conductor.

6. The quality detection device according to claim 5, wherein the integrated circuit comprises a programmable logic controller (PLC) module configured to transmit data and relays forming the switching modules; the PLC module is respectively connected with the driving module, the collecting module, and a plurality of relays; each relay is connected with two driving ends and two collecting ends, and the two driving ends are disposed in pairs with and the two collecting ends.

7. The quality detection device according to claim 1, wherein the driving module and the collecting module are integrated into a micro resistance meter; the micro resistance meter comprises a driving system and a collecting system; the driving system is configured to output current and connect with the driving module; and the collecting system is configured to collect electrical information and connects with the collecting module.

8. A quality detecting method based on a welded seam, comprising steps:

respectively abutting integrated probe assemblies in pairs against two sides of a welded seam on a conductor, wherein the integrated probe assemblies are disposed in pairs and each of the integrated probe assemblies comprises a driving end and a collecting end, the driving end of one integrated probe assembly is matched with the driving end of another integrated probe assembly disposed in pairs with the one integrated probe assembly; and the collecting end of one integrated probe assembly is matched with the collecting end of another integrated probe assembly disposed in pairs with the one integrated probe assembly;

releasing a current to form a current loop between a conductor and the driving ends abutting against the conductor;

abutting collecting ends against the conductor, obtaining an electrical information of an area of the current loop formed in the conductor, and forming a plurality of scanning channels; and converting the collected electrical information into a resistance value and obtaining quality of the welded seam;

wherein step of determining the quality of the welded seam comprises:

pre-determining a first ratio interval, a second ratio interval and a third ratio interval, where the first ratio interval, the second ratio interval, and the third ratio interval are sorted by ascending values;

calculating a ratio of an obtained resistance value and a resistance value of the conductor itself; and if the ratio is in the first ratio interval, the welded seam is considered to be qualified; if the ratio is in the second ratio interval, the welded seam is considered to be false welding; if the ratio is in the third ratio interval, the welded seam is considered to be poor welding.

9. The quality detecting method according to claim 8, wherein the steps of the quality detecting method further comprise:

collecting a voltage value of the area of the current loop corresponding to the collecting end by the collecting end and obtaining a resistance value of a position corresponding to the area of the current loop according to an electrified current value; and determining whether the resistance value is abnormal or not, if the resistance value is normal, the welded seam is considered to be qualified, otherwise the welded seam is considered to be defective.

\* \* \* \* \*